US00PP10486P

United States Patent [19]

Jepsen

[11] Patent Number: Plant 10,486

[45] Date of Patent: Jul. 7, 1998

[54] KALANCHOE PLANT NAMED 'CAROLINE'

[75] Inventor: Knud Jepsen, Hinnerup, Denmark

[73] Assignee: Knud Jepsen A/S, Hinnerup, Denmark

[21] Appl. No.: 760,366

[22] Filed: Dec. 4, 1996

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—C. A. Whealy

[57] ABSTRACT

A distinct cultivar of Kalanchoe plant named 'Caroline', characterized by its numerous purple flowers and flower buds; green leaves; and good postproduction longevity.

2 Drawing Sheets

1

The present invention relates to a new and distinct cultivar of Kalanchoe plant, botanically known as *Kalanchoe blossfeldiana*, and hereinafter referred to by the cultivar name Caroline.

The new cultivar is a product of a planned breeding program conducted by the inventor in Hinnerup, Denmark. The objective of the breeding program was to create a new Kalanchoe cultivar having purple flowers, green leaves and rapid growth and flowering rate.

The new cultivar originated from a cross made by the inventor of the Kalanchoe cultivar Isabella (disclosed in U.S. Plant Pat. No. 9,427) as the male or pollen parent with the nonpatented cultivar Denise as the female or seed parent. The cultivar Caroline was discovered and selected by the inventor as a flowering plant within the progeny of the stated cross in a controlled environment in Hinnerup, Denmark. Asexual reproduction of the new cultivar by terminal cuttings taken as Hinnerup, Denmark, has shown that the unique features of this new Kalanchoe are stable and reproduced true to type in successive generations.

The cultivar Caroline has not been observed under all possible environmental conditions. The phenotype may vary somewhat with variations in environment such as temperature, daylength and light intensity, without, however, any variance in genotype.

The following observations, measurements and comparisons describe plants grown in Hinnerup, Denmark, under commercial practice in a glass-covered greenhouse.

The following traits have been repeatedly observed and are determined to be the unique characteristics of 'Caroline'. These characteristics in combination distinguish 'Caroline' as a new and distinct cultivar:

1. Numerous purple flowers and flower buds.
2. Green leaves.
3. Good postproduction longevity.

The new cultivar is most similar to the cultivar Isabella. However plants of the new cultivar differ from plants of the cultivar Isabella by its darker flower color, smaller flowers and more numerous flower buds.

The accompanying colored photographs illustrates the overall appearance of the new cultivar, showing the colors as true as it is reasonably possible to obtain in colored reproductions of this type. The photographs were taken under diffuse natural light conditions on an overcast day with electronic flash at approximately noon in Hinnerup, Denmark. The photograph on the first sheet comprises a side perspective view of a typical potted plant of 'Caroline'. The photograph at the top of the second sheet comprises a top perspective view of a typical potted plant of 'Caroline' showing the flowers. The photograph at the bottom of the second sheet comprises from left to right: top perspective view of a typical flowering cyme; side perspective view of a typical flowering cyme; side perspective view of an individual flower; immature leaves, abaxial (top) and adaxial (bottom) surfaces; and fully mature leaves, abaxial (top) and adaxial (bottom) surfaces. Flower and foliage colors in the photographs may appear different from the actual colors due to light reflectance.

2

In the following description, color references are made to The Royal Horticultural Society Colour Chart except where general terms of ordinary dictionary significance are used.

Botanical classification: *Kalanchoe blossfeldiana* cultivar Caroline.

Parentage:

*Male or pollen parent.*—*Kalanchoe blossfeldiana* cultivar Isabella (disclosed in U.S. Plant Pat. No. 9,427).

*Female or seed parent.*—*Kalanchoe blossfeldiana* cultivar Denise (not patented).

Propagation:

*Type cutting.*—Terminal cuttings.

*Time to initiate roots.*—About ten days.

*Rooting habit.*—Numerous, fine, fibrous, and well-branched.

Plant description:

*Form.*—Upright and compact; plant shape is columnar or an inverted triangle with a rounded apex. Actual plant shape will depend on whether or not plants are pinched (vegetative terminals removed). Appropriate for 9 to 10 -cm containers with one cutting per container, not pinched; for 13-cm containers with three cuttings per container, not pinched; or for 13-cm containers with one cutting, pinched.

*Branching habit.*—Freely branching, generally shoots formed at every node.

*Plant height at flowering.*—About 25 cm.

*Plant diameter at flowering.*—About 20 cm.

*Foliage description.*—Leaves simple, opposite, generally symmetrical. Size: Leaf size is reduced after floral induction. Vegetative plants: Length: About 10 cm. Width: About 8 cm. Reproductive plants: Length: About 6 cm. Width: About 3.5 cm. Shape: Oval. Apex: Obtuse. Base: Obtuse. Margin: Undulate. Texture: Leathery, glabrous, and succulent. Aspect: Undulating or slightly cupped. Color: Young foliage upper side: 137A. Young foliage under side: 137B. Mature foliage upper side: 137A. Mature foliage under side: 137B.

Flower description:

*Flower type and habit.*—Single flowers arranged in compound dichasial cymes. The main inflorescence are branched into one primary and 2 to 4 minor cymes during development. Freely flowering. Flowers persistent.

*Nature flowering season.*—Late autumn/winter/early spring; flower initiation and development can be induced under short day/long night conditions.

*Inflorescence borne.*—Above foliage, arising from leaf axils.

*Time to flower.*—In the summer with 20C growing temperatures, about 8 weeks of short day/long night conditions are required to produce flowering plants. During the winter with supplemental lighting and 20C growing temperatures, about 9 weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About 1.5 weeks after the first flower has opened, 50% of the remaining flowers are open.

*Flower diameter.*—About 2.1 cm.

*Quantity.*—On unpinched plants, at least 250 flowers per plant.

*Flower buds.*—Shape: Narrowly oblong. Size: Length: About 1.5 cm. Width: About 3 mm. Color: 63A.

*Petals.*—Quantity: Four fused at base to form bell-shaped corolla. Length: About 8 mm. Shape: Round obovate. Apex: Cuspidate. Margin: Entire. Texture: Glabrous, smooth and satiny. Color: When opening: 74A. Mature, upper side: 74A/74B. Mature, under side: 74C. Fading to: 74B.

*Reproductive organs.*—Stamens. Stamen number: Eight. Filament color: Yellow green. Pollen color: Yellow. Pistils: Pistil number: Four. Style color: White. Stigma shape: Round. Ovaries: Hypogenous and four-celled. Ovary size: 5 by 1 mm. Ovary color: Light green.

Disease resistance: No known Kalanchoe diseases observed to date under commercial practice.

Seed production: Seed production has not been observed.

It is claimed:

1. A new and distinct cultivar of Kalanchoe plant named 'Caroline', as illustrated and described.

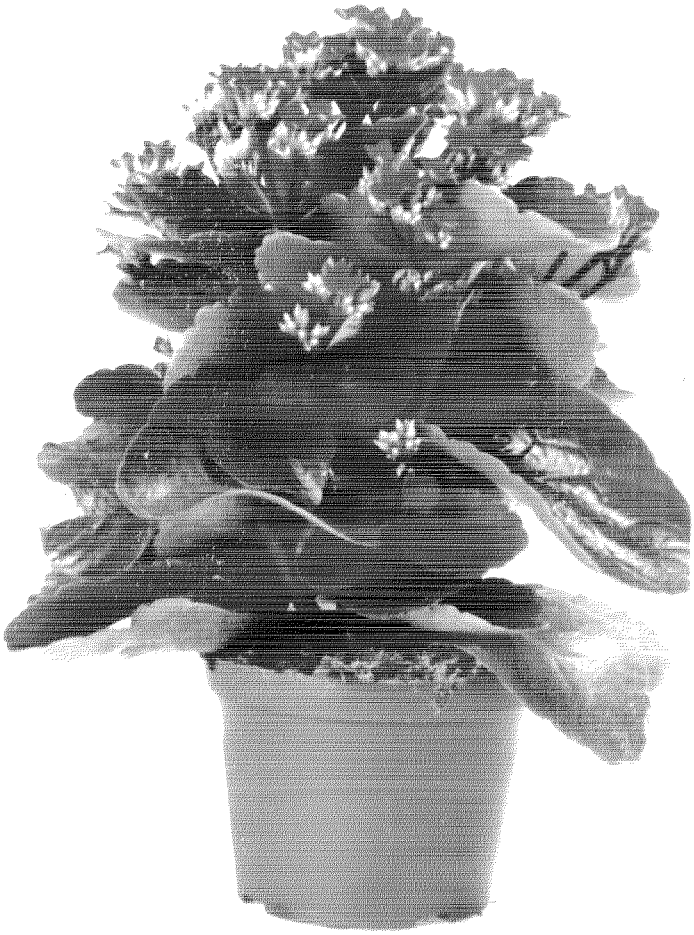

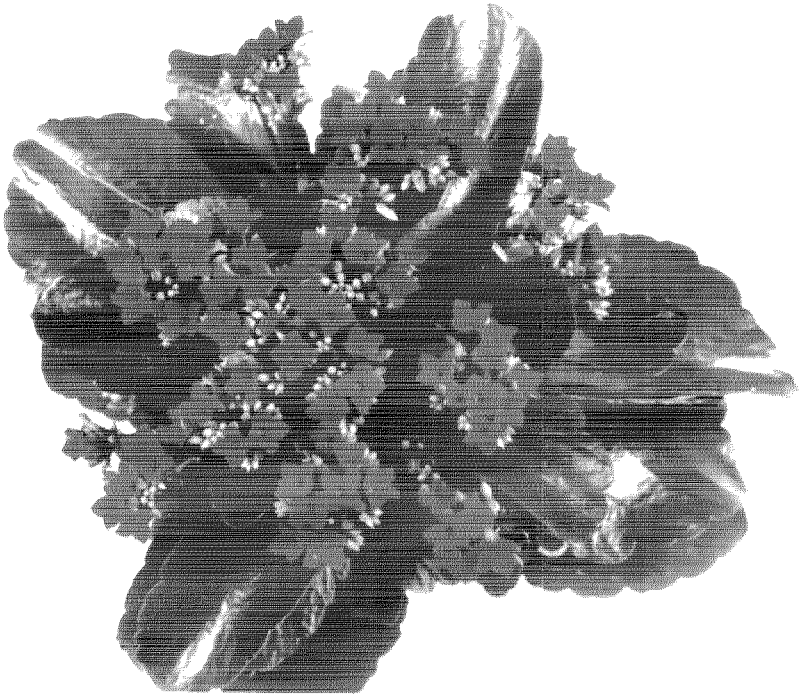
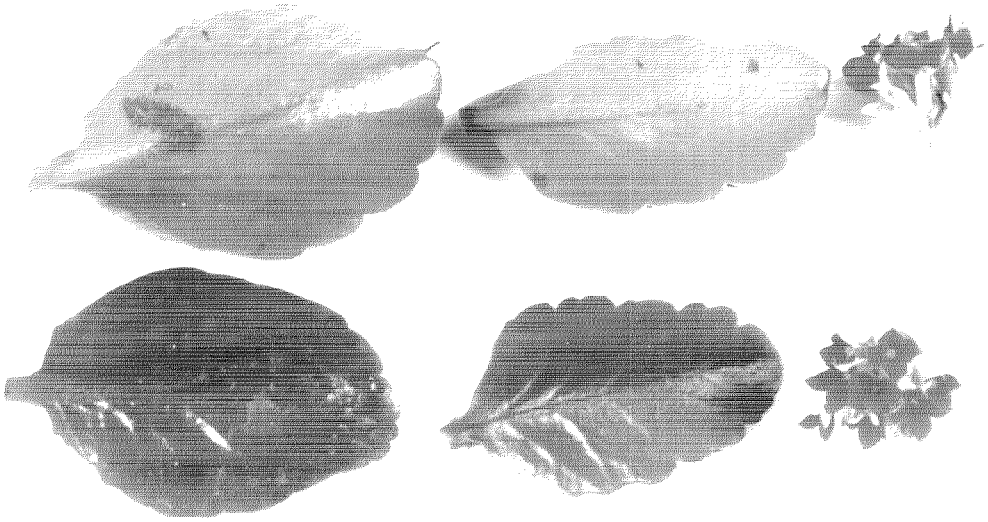

* * * * *